United States Patent [19]

Jansen et al.

[11] Patent Number: 4,863,965
[45] Date of Patent: Sep. 5, 1989

[54] IBUPROFEN ACID ANHYDRIDES AND PRODRUG PHARMACEUTICAL COMPOSITION CONTAINING THE SAME

[75] Inventors: Frans H. J. Jansen, Oud Turnhout; Etienne J. De Cock, Grimbergen, both of Belgium

[73] Assignee: B.V.B.A. Inpharm, Oud Turnhout, Belgium

[21] Appl. No.: 863,131

[22] Filed: May 14, 1986

[30] Foreign Application Priority Data

May 15, 1985 [NL] Netherlands ............... 8501408

[51] Int. Cl.$^4$ .................. A61K 31/19; C07C 57/34
[52] U.S. Cl. .................. 514/576; 514/578; 514/556; 514/553; 562/887
[58] Field of Search ............ 260/546, 548, 549; 514/576

[56] References Cited

U.S. PATENT DOCUMENTS 2,577,699  12/1951  Cooper .................. 540/342
4,206,220   6/1980  Sloan ................... 514/419

FOREIGN PATENT DOCUMENTS 42-3774  2/1967  Japan .

OTHER PUBLICATIONS

March, Advanced Organic Chemistry: Reactions, Mechanisms, and Structure, McGraw Hill, 1968, p. 325.

*Primary Examiner*—Mary C. Lee
*Assistant Examiner*—Mary Sue Howard
*Attorney, Agent, or Firm*—Bert J. Lewen; Henry Sternberg

[57] ABSTRACT

Pharmaceutical compositions of the prodrug type, a process for the preparation thereof, a process for the preparation of the as prodrug functioning compounds and compounds obtained herein.

The pharmaceutical compositions of the invention contain organic acid anhydrides with formula 1 through 5, as well as the pharmacological acceptable salts thereof as prodrug functioning compounds, together with a suitable pharmaceutically acceptable gaseous, liquid or solid carrier.

The prodrug systems of the invention possess as favorable property that they amend the residence time of the pharmaceutical composition in the body by influencing the transport system.

Furthermore they increase the biological availability because of the more lipophilic properties of the anhydride compared with the acid, so that this improved administration performance may contribute to lower dosages.

Further the prodrug systems according to the invention contribute to the reduction of the complaints of patients, because the systems usually remove the unpleasant bitter taste and the flavor, whereas the gastro intestinal irritation of the organic acids is removed or reduced.

4 Claims, No Drawings

IBUPROFEN ACID ANHYDRIDES AND PRODRUG PHARMACEUTICAL COMPOSITION CONTAINING THE SAME

The invention relates to pharmaceutical compositions of the prodrug type, to a process for the preparation of such compositions, to a process for the preparation of the as prodrug functioning compounds, and to the compounds obtained herein.

Under pharmaceutical compositions of the prodrug type there are to be understood compositions, which are administered orally or transdermally, wherein besides an improved lipophilicity an improved absorption and penetration is obtained.

The most important representatives of the known and used prodrug systems of organic acids are of the ester type.

Some known examples thereof are the esters of ampicillin, to wit pivampicillin, (the pivaloyloxymethyl ester of ampicillin,-cf. E. K. Frederiksen, WO Godfredsen, South African patent specification No. 68.05952 (1969) and U.S. patent specification No. 3,660,575 (1972) in the name of von Daehne et al, J. Med. Chem. 13, 607 (1970)), bacampicillin (the ethoxy carbonyl oxyethyl ester of ampicillin-cf. No. B. A. Ekstrom, B. O. H. Sjoberg, German patent specification 2,144,457 (1972), U.S. patent specification No. 3,873,521 (1975) and U.S. patent specification No. 3,939,270 (1976) and talampicillin (the phthalidyl ester of ampicillin-cf. Murakami et al German patent specification No. 2.225.149 (1972) and U.S. patent specification No. 3,951,954 (1976), Ferres Clayton, German patent specifications No. 2.228.012 (1972) and 2.228.255 (1972) and U.S. patent specification No. 3,860,579 (1975)).

It should be understood that U.S. patent specification No. 3,646,201 discloses prodrug systems too. As prodrug functioning compound always use is made of a carbonate of acetyl salicylic acid. Such aspirin prodrug systems possess a number of advantages compared with acetyl salicylic acid, such as the extended activity period and the elimination of gastro intestinal irritation, which otherwise often may result in acute intestinal bleedings, according to the U.S. patent specification.

In general prodrug derivatives of a certain medicine are prepared in order to modify certain unwanted properties of the medicine (see A. A. Sinkula, Ann. Rep. Med. Chem. 10, 306 (1975). The actual medicine is released in vivo.

An important disadvantage of the known prodrug systems is that it is rather voluminous compared with the starting medicine, e.g. the formerly mentioned ampicillin, resulting for instance in the use of huger tablets. It is generally known that patients often have problems with the swallowing of tablets. In certain cases this conventional prodrug technique results in such voluminous tablets, that the swallowability of a certain unit dose becomes difficult.

There are known the neutral symmetric cephalosporin anhydrides (U.S. patent specification No. 3,763,152, M. Wolf et al), wherein it is stated, that these anhydrides are novel antibiotic active anhydrides of cephalosporan acid derivatives, as well as the mixed anhydrides of penicillin derivatives (D. E. Cooper, U.S. patent specification No. 2,577,699; Galenika Pharm. Chem. Ind., German patent specification No. 2.126.037; Glaxo, Dutch patent application No. 7203191), which on the one hand may be used as intermediates in the synthesis of penicillin and cephalosporin derivatives and on the other hand they posses an antibiotic activity, as aqueous slurry, or they intend to extend the activity after the intramuscular injection.

This type of administration is, however, not very patient friendly, since the intramuscular injections usually will be experienced as painful.

Furthermore is known an oral or topical use of esters of phenyl acetic acid derivatives, a.o. of ibuprofen, (Hisamitsu Pharmaceutical Co., Dutch patent application No. 7614303), but the analgetic, anti pyretic and anti-inflammatory activity of these esters is significantly lower than that of ibuprofen.

The invention aims now to provide prodrug systems wherein the above-mentioned disadvantages are removed efficiently. The derivatives according to the invention are more active and they are furthermore convenient for the patient because of the way of administration, to wit orally or transdermally.

The invention provides now pharmaceutical compositions of the prodrug type, characterized in that the said compositions contain organic acid anhydrides with formula 1 through 5, as well as the pharmacological acceptable salts thereof as prodrug functionating compounds, together with a suitable pharmaceutically acceptable gaseous, liquid or solid carrier.

The pharmaceutical compositions of the prodrug type according to the invention may be formulated as such into tablets, dragees, capsules, gelules, suppositories, aerosol containers with inert carrier gases, such as fluoro hydrocarbons, nitrogen, air, laughing gas, for transdermal applications or dosage aerosol containers for transbuccal applications.

It should be understood that the organic acid anhydrides having formulas 1 through 5 are new compounds.

Surprisingly it has been found that the pharmaceutical compositions according to the invention, containing an organic acid anhydride of the active acid as prodrug functioning compound, have a volume, which is less than half of that of the starting acid. This means, that the volume of the pharmaceutical composition which is to be administered is essentially less than in the case that the composition should contain the active acid as such.

This means that the pharmaceutical compositions according to the invention are essentially more administration friendly than the usual prodrug systems.

The present invention is to be considered as a genus invention, to wit the use of pharmacologically active organic acids in the form of their acid anhydrides as prodrug systems.

Such acid anhydride prodrug systems possess furthermore as favourable property that they amend the residence time of the pharmaceutical composition in the body by influencing the transport system.

Furthermore they increase the biological availability because of the more lipophilic properties of the anhydride compared with the acid, so that this improved administration performance may contribute to lower dosages.

Further the prodrug systems according to the invention contribute to the reduction of the complaints of patients, because the systems usually remove the unpleasant bitter taste and the flavour, whereas the gastro intestinal irritation of the organic acids is removed or reduced.

Furthermore they allow to process certain existing medicines to pharmaceutical compositions in a more convenient way, because for instance the addition of acid neutralising agents in the form of salts, sodium, potassium, calcium, or in the form of inorganic or organic bases is superfluous.

The present pharmaceutical compositions are in itself pharmacologically inactive. They become active as soon as the corresponding active acid is released in the blood or in the tissue by hydrolysis.

The present prodrug system enables furthermore a more uniform and in the time extended activity of the medicine, partly because of the hydrolysis of the anhydride and partly because the anhydride may be formulated to pharmaceutical compositions possessing retarded or controlled release of the active acid.

Finally the invention enables that all types of pharmacological active organic acids may be processed more efficiently and faster to suitable new medicines.

A very favourable representative of the symmetric anhydrides according to the invention is ibuprofen acid anhydride with formula 1

$$\left( R_2 \underset{\displaystyle\phantom{x}}{\underset{\displaystyle\phantom{x}}{\bigcirc}} \underset{O}{\overset{R_1}{\underset{\|}{\text{C}}}} \text{O} \right)_2 \quad 1$$

wherein $R_1$ represents a methyl group and $R_2$ is an isobutyl group.

Other favourable symmetric anhydrides according to the invention are valproic acid anhydride with formula 2, $$\left( \underset{R_4}{\overset{R_3}{\diagdown}} \underset{\phantom{x}}{\overset{H}{\underset{|}{\text{C}}}} \underset{\phantom{x}}{\overset{O}{\underset{\|}{\text{C}}}} \text{O} \right)_2 \quad 2$$

wherein $R_3$ and $R_4$ are the same and represent a n-propyl group, ampicillin anhydride-dihydrochloride with formula 3, $$3$$

amoxicillin anhydride-dihydrochloride with formula 4

$$4$$

and ursodeoxycholic acid anhydride with formula 5

$$5$$

It should be understood that the invention is not limited to the anhydrides with formula 1 through 5.

Another interesting symmetric organic acid anhydride is captopril anhydride, i.e. 1-(3-mercapto-2-methyl-1-oxopropyl)-L-proline anhydride, possessing antihypertensive activity, as well as the analogues thereof.

The pharmaceutical compositions according to the invention roughly may be distinguished in:

(a) non steroidal anti-inflammatory compositions

This comprises a series of organic acids with the above formula 1, wherein $R_1$ is hydrogen or a $C_1$-$C_3$ alkyl group and $R_2$ represents an aliphatic, a cyclic, an aromatic or hetero aromatic group, an aniline or etheric group, or $R_2$ represents halogens, without steroidal structure and possess an anti inflammatory activity. An example of these compositions is the above-mentioned ibuprofen acid anhydride with the above formula 1, wherein $R_1$ is a methyl group and $R_2$ is an isobutyl group, which may be described as a phenyl acetic acid derivative.

(b) anti-epileptica

Of the compounds of the above formula 2, wherein $R_3$ and $R_4$ are identical or different and stand for aliphatic or cyclic alkyl groups, the above-mentioned valproic acid anhydride is an example, wherein $R_3$ and $R_4$ each represent a n-propyl group.

(c) antibiotics

Under the antibiotics may be particularly mentioned β-lactam antibiotics of the pencillin type. Examples hereof are penicillin V anhydride, ampicillin anhydride dihydrochloride with the above formula 3 and amoxicillin anhydride dihydrochloride with the above formula 4.

(d) steroids

Ursodeoxycholic acid anhydride with the above formula 5.

Furthermore the invention relates to a process for the preparation of the pharmaceutical compositions, characterized in that the as prodrug functioning organic acid anhydrides with the above formula 1 through 5 are brought into a for therapeutic purposes suited administration form together with a pharmaceutically acceptable gaseous, liquid or solid carrier.

The pharmaceutical compositions of the prodrug type may be formulated into tablets, dragees, capsules, gelules, suppositoria, aerosol containers with inert propellant gases, such as fluoro hydrocarbons, nitrogen, air, laughing gas, . . . for transdermal application or dosage aerosol containers for transbuccal application.

Finally the invention relates to a process for the preparation of the as prodrug functioning compounds for use in the pharmaceutical compositions and in the process for the preparation thereof, characterized in that the as prodrug functioning compounds organic acid anhydrides are prepared, by converting the corresponding acids into the symmetric anhydride in a manner which is known in itself.

Of course the invention comprises the obtained organic acid anhydrides.

The invention will be further explained by means of the following examples, without any restriction of the invention thereto.

EXAMPLE I

Preparation of ibuprofen acid anhydride with the above formula 1 ($R_1$=Me, $R_2$=iBu)

500 g (2,43 mol) of ibuprofen was added to a three neck round bottom flask of 2 liters, which was provided with a vigreux-column with a distillation unit. Then 400 ml of freshly distilled xylene and 138 ml acetic acid anhydride were added. The obtained mixture was refluxed during 5 hours, whereupon the formed acetic acid was distilled slowly.

After cooling the solution was filtrated and distilled under reduced pressure.

The ibuprofen anhydride was obtained at 155° C. (2 mm Hg, 270 Pa) in a yield of 90% and with a molecular weight of 394.53 g/mol.

Thin layer chromatography data:

TLC ($SiO_2/CHCl_3$) Rf=0.72. Infrared spectrum Ir (NaCl): 3125, 3100, 3150, 3120, 2950, 2930, 2870, 2850, 1817, 1750, 1710, 1510, 1460, 1100, 1030, 1020, 845, 800 $cm^{-1}$.

NMR resonance spectrum:

NMR (60 MHz, $CDCl_3$): =0,92 (12H, d), 1,40 (6H, d), 1,83 (2H, m), 2,46 (4H, d), 3,63 (2H, q), 7,03 (8H, s) (in ppm values).

Mass spectrum:

MS (FAB, Neg): m/z=413, 412, 411, 297, 235, 217, 204, 205, 183, 173, 175, 173, 171, 161, 117, 99, 97, 91, 73, 59, 49, 36.

EXAMPLE II

Preparation of valproic acid anhydride with the above formula 2. ($R_3$=$R_4$=n−Pr)

288 g (2 mol) of 2-propyl pentanoic acid was added to a three neck round bottom flask of 1 liter, which was provided with a vigreux column with distillation unit. Then 330 ml of freshly distilled xylene and 120 ml acetic acid anhydride were added. The obtained mixture was refluxed during 5 hours whereupon the formed acetic acid was slowly distilled. After cooling the solution was filtrated and distilled under reduced pressure.

The 2-propyl pentanoic acid anhydride was obtained at 155°–156° C. (14 mm Hg, 1,9 kPa) in a yield of 89% and with a molecular weight of 270.42 g/mol.

The thus obtained valproic acid anhydride should be considered as a prodrug of valproic acid. Valproic acid possesses anti-epileptic properties, but has a side effect gastro-intestinal complaints, such as nausea, vomica and indigestion.

EXAMPLE III

Preparation of ampicillin anhydride.dihydrochloride with the above formula 3

A tetrahydrofuran solution (400 ml) of mono-trimethyl silylacetamide (MSA) (90 g, 0.68 mol) was stirred at room temperature, followed by the addition of 6-amino penicillin acid (37.2 g, 0.172 mol). The mixture was stirred under heating until a homogeneous solution was obtained.

A tetrahydrofuran solution (600 ml) of iso-butyl-chloroformate (22.6 ml, 0.172 mol) was cooled to −10° C., whereupon a mixture of D(−)-tert.butyloxycarbonylphenyl glycine (43.2 g, 0.172 mol) and triethylamine (24 ml, 0.172 mol) in tetrahydrofuran (200 ml) with 20 drops N,N-dimethyl-benzylamine added thereto, was dripped slowly.

After completion of the addition the mixture was stirred during 1 hour at −10° to −20° C. The trimethyl sililated mixture was added all at once to the mixed anhydride, followed by stirring druing 2 hours at −10° to −20° C. and then further during 18 hours at room temperature.

The mixture was filtrated, whereupon the filtrate was distilled under reduced pressure. The residu was solved in ethyl acetate followed by washing with 1N HCl (twice) and with a saturated aqueous NaCl solution (twice). The ethyl acetate solution was concentrated under vacuum, whereupon the obtained material was recrystallized. This material was pure enough in order to use it in the following step.

20 g (44.5 mmol) of tert.butyloxycarbonyl-ampicillin in 150 ml tetrahydrofuran was added dropwise to a solution of 7.94 g (49 mmol) of 1,1′-carbonyldiimidazole at −10° C. This solution was stirred as long as no gas development could be observed.

Meanwhile 20 g (44 mmol) of tert.butyl oxycarbonylampicillin in 150 ml dry dimethylformamide was stirred in the presence of anhydrous potassium carbonate (24.3 g, 176 mmol) during 3 hours at room temperature.

This last mentioned solution was added dropwise to the tetrahydrofuran solution, whereupon the obtained mixture further was stirred during 18 hours at room temperature after the addition was completed.

The solution was completely evaporated under reduced pressure. The residu was taken up in ether (300 ml) and washed with 1N HCl (twice) and with water (to neutral). The ether solution was dried over magnesium sulphate, filtrated and then treated with HCl-gas under ice cooling. The formed hydrochloride salt was separated by filtration. The ampicillin anhydride-dihydrochloride with the above formula 3 was obtained.

EXAMPLE IV

Preparation of amoxicillin anhydride.dihydrochloride with the above formula 4

Analogous with example III, provided that the D(−)-tert-butyloxycarbonylphenylglycine was replaced by D(−)-tert.butyloxycarbonyl (4-tert.-butyloxyphenyl)-glycine.

EXAMPLE V

Preparation of ursodeoxycholic acid anhydride with the above formula 5

In an analogous way ursodeoxycholic acid anhydride with the above formula 5 was prepared, starting from the dibenzyloxycarbonyl protected derivative, from which the protecting group was splitted off by hydrogenolysis.

We claim:

1. An organic acid anhydride having the formula

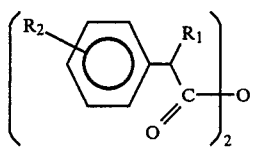

wherein $R_1$ is hydrogen or a $C_1$ to $C_3$ alkyl group and $R_2$ is an isobutyl group or a pharmaceutically acceptable salt thereof.

2. The organic acid anhydride of claim 1 wherein $R_1$ is a methyl group and $R_2$ is an isobutyl group.

3. A non-steroidal anti-inflammatory prodrug composition which comprises an organic acid anhydride having the formula

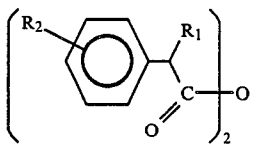

wherein $R_1$ is hydrogen or a $C_1$ to $C_3$ alkyl group and $R_2$ is an isobutyl group or a pharmaceutically acceptable salt thereof in combination with a pharmaceutically acceptable carrier, said organic acid anhydride being present in an amount sufficient to form a pharmaceutically effective amount of the corresponding organic acid in vivo.

4. The prodrug composition of claim 3 wherein $R_1$ is a methyl group and $R_2$ is an isobutyl group.

* * * * *